(12) United States Patent
Lin et al.

(10) Patent No.: US 10,492,755 B2
(45) Date of Patent: Dec. 3, 2019

(54) CALIBRATION PHANTOM COMPRISING A REFLECTANCE CALIBRATION TARGET AND A PLURALITY OF RADIO-OPAQUE MARKERS

(71) Applicant: Carestream Health, Inc., Rochester, NY (US)

(72) Inventors: Yuan Lin, Rochester, NY (US); William J. Sehnert, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 214 days.

(21) Appl. No.: 15/469,655

(22) Filed: Mar. 27, 2017

(65) Prior Publication Data

US 2018/0014809 A1  Jan. 18, 2018

Related U.S. Application Data

(60) Provisional application No. 62/361,534, filed on Jul. 13, 2016.

(51) Int. Cl.
*A61B 6/00* (2006.01)
*A61B 6/03* (2006.01)
*A61B 6/14* (2006.01)

(52) U.S. Cl.
CPC .............. *A61B 6/583* (2013.01); *A61B 6/032* (2013.01); *A61B 6/035* (2013.01); *A61B 6/14* (2013.01); *A61B 6/4085* (2013.01); *A61B 6/44* (2013.01); *A61B 6/4417* (2013.01); *A61B 6/461* (2013.01); *A61B 6/501* (2013.01); *A61B 6/58* (2013.01); *A61B 6/582* (2013.01); *A61B 6/584* (2013.01)

(58) Field of Classification Search
CPC .......... A61B 6/032; A61B 6/035; A61B 6/14; A61B 6/4417; A61B 6/501; A61B 6/58; A61B 6/582; A61B 6/583; A61B 6/584; A61B 6/44
USPC ................... 378/20, 38–40, 207, 4, 196–198
See application file for complete search history.

(56) References Cited

U.S. PATENT DOCUMENTS

| | | | | |
|---|---|---|---|---|
| 5,442,674 A | * | 8/1995 | Picard | A61B 6/583 378/18 |
| 5,841,830 A | * | 11/1998 | Barni | A61B 6/032 378/15 |
| 6,428,547 B1 | * | 8/2002 | Vilsmeier | A61B 5/06 600/424 |
| 6,493,574 B1 | * | 12/2002 | Ehnholm | A61B 5/055 378/18 |

(Continued)

FOREIGN PATENT DOCUMENTS

| WO | 2013/185011 | 12/2013 |
|---|---|---|
| WO | 2016/003957 A2 | 1/2016 |

OTHER PUBLICATIONS

Commonly assigned U.S. Appl. No. 15/165,159, entitled: System and Method for Motion Artifacts Reduction filed May 26, 2016, by Lin et al.

(Continued)

*Primary Examiner* — Allen C. Ho

(57) ABSTRACT

A calibration phantom has a surface having a reflectance calibration target with a pattern that is indicative of one or more spatial reference positions. Radio-opaque markers are disposed in the calibration phantom and are positionally correlated to the one or more spatial reference positions of the reflectance calibration target.

19 Claims, 12 Drawing Sheets

(56) References Cited

U.S. PATENT DOCUMENTS

| | | | |
|---|---|---|---|
| 6,527,443 B1* | 3/2003 | Vilsmeier | A61B 6/12 378/205 |
| 6,585,412 B2* | 7/2003 | Mitschke | A61B 6/547 378/207 |
| 6,694,168 B2* | 2/2004 | Traxel | A61B 90/39 600/300 |
| 7,010,095 B2* | 3/2006 | Mitschke | A61B 90/36 378/162 |
| 7,510,325 B2* | 3/2009 | Endo | A61B 6/032 250/252.1 |
| 7,643,615 B2* | 1/2010 | Wang | G03B 42/02 378/162 |
| 7,643,862 B2* | 1/2010 | Schoenefeld | A61B 90/36 600/407 |
| 7,689,014 B2* | 3/2010 | Abovitz | A61B 6/022 382/128 |
| 7,712,961 B2* | 5/2010 | Hörndler | A61B 6/12 378/207 |
| 7,755,031 B2* | 7/2010 | Jang | A61B 6/5276 250/252.1 |
| 7,780,351 B2* | 8/2010 | Heigl | A61B 6/032 378/207 |
| 7,822,172 B2* | 10/2010 | Rührnschopf | G01N 23/04 378/19 |
| 7,840,256 B2* | 11/2010 | Lakin | A61B 34/20 408/147 |
| 7,844,094 B2* | 11/2010 | Jeung | A61B 6/583 382/131 |
| 7,907,699 B2* | 3/2011 | Long | A61N 5/1049 378/65 |
| 7,922,391 B2* | 4/2011 | Essenreiter | A61B 6/4441 378/205 |
| 7,967,507 B2* | 6/2011 | Levine | G03B 42/047 378/163 |
| 8,007,173 B2* | 8/2011 | Paidi | A61B 6/584 378/207 |
| 8,043,003 B2* | 10/2011 | Vogt | G01N 23/046 378/207 |
| 8,104,958 B2* | 1/2012 | Weiser | A61B 6/583 378/162 |
| 8,165,659 B2* | 4/2012 | Sheffer | A61B 90/36 600/407 |
| 8,198,579 B2* | 6/2012 | Jeung | A61B 6/08 250/252.1 |
| 8,220,994 B2* | 7/2012 | Heigl | A61B 6/547 378/207 |
| 8,309,910 B2* | 11/2012 | Dutta | A61B 6/032 250/252.1 |
| 8,311,365 B2* | 11/2012 | Chen | G06T 7/74 378/163 |
| 8,313,238 B2* | 11/2012 | Takahashi | A61B 6/583 378/205 |
| 8,359,085 B2* | 1/2013 | Hörndler | A61B 6/032 378/205 |
| 8,571,637 B2* | 10/2013 | Sheffer | A61B 34/20 128/845 |
| 8,737,708 B2* | 5/2014 | Hartmann | A61B 6/12 382/128 |
| 8,768,026 B2* | 7/2014 | Ren | A61B 6/0414 382/131 |
| 8,777,485 B2* | 7/2014 | Holt | A61B 6/03 250/252.1 |
| 8,891,849 B2* | 11/2014 | Rohler | A61B 6/032 382/132 |
| 8,895,912 B2* | 11/2014 | Coolens | A61B 6/583 250/252.1 |
| 8,948,471 B2* | 2/2015 | Fichtinger | A61B 6/504 382/128 |
| 9,044,190 B2* | 6/2015 | Rubner | A61B 6/4405 |
| 9,305,354 B2* | 4/2016 | Burlon | A61B 6/583 |
| 9,336,597 B2* | 5/2016 | Daon | A61B 90/39 |
| 9,526,471 B2* | 12/2016 | Goodenough | A61B 6/025 |
| 9,610,056 B2* | 4/2017 | Lavallee | A61B 6/032 |
| 9,672,607 B2* | 6/2017 | Demri | A61B 5/7425 |
| 9,681,851 B2* | 6/2017 | Rohler | A61B 6/482 |
| 9,867,588 B2* | 1/2018 | Amiri | A61B 6/4405 |
| 10,010,372 B1* | 7/2018 | Beck | A61B 6/505 |
| 10,022,104 B2* | 7/2018 | Sell | G01R 33/58 |
| 10,028,720 B2* | 7/2018 | Lin | A61B 6/032 |
| 10,034,648 B2* | 7/2018 | Lin | A61B 6/527 |
| 10,119,922 B2* | 11/2018 | Bernard | A61B 6/032 |
| 10,169,845 B2* | 1/2019 | Sakaguchi | A61B 6/5258 |
| 2008/0095302 A1 | 4/2008 | Ruhrnschopf et al. | |

OTHER PUBLICATIONS

Z. Zhang, "A Flexible New Technique for Camera Calibration", IEEE Transactions on Pattern Analysis and Machine Intelligence, vol. 22, No. 11, 2000, pp. 1330-1334.

S. Zhang et al., "Novel Method for Structured Light System Calibration", Optical Engineering, vol. 45(8), 2006, pp. 083601-1-083601-8.

P. Tavares et al., "Linear Calibration Procedure for the Phase-To-Height Relationship in Phase Measurement Profilometry", Optics Communications 274, 2007, pp. 307-314.

X. Li et al., "A Generic Geometric Calibration Method for Tomographic Imaging Systems With Flat-Panel Detectors—A Detailed Implementation Guide", Medical Physics, vol. 37, No. 7, 2010, pp. 3844-3854.

* cited by examiner

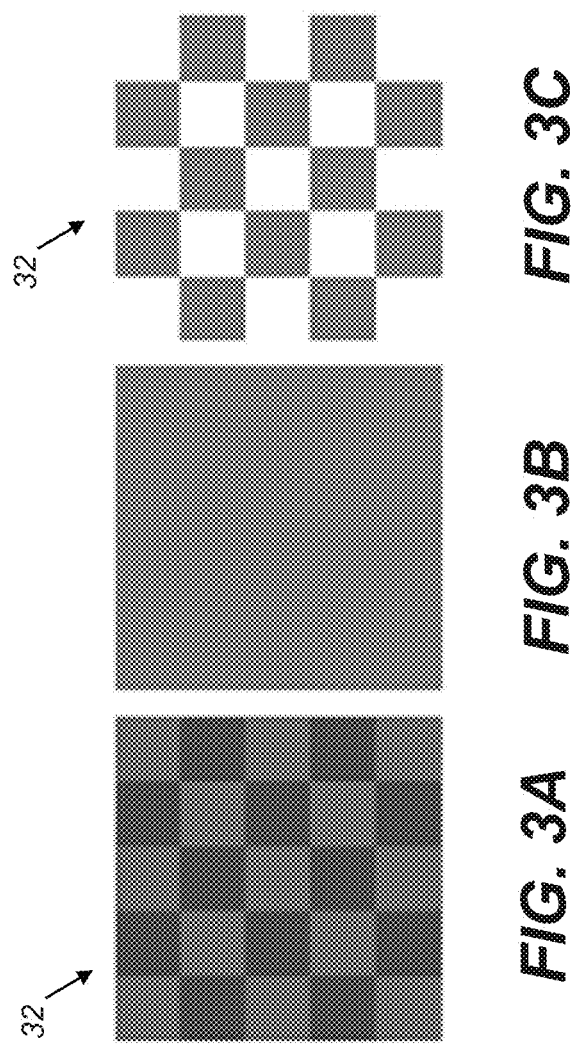

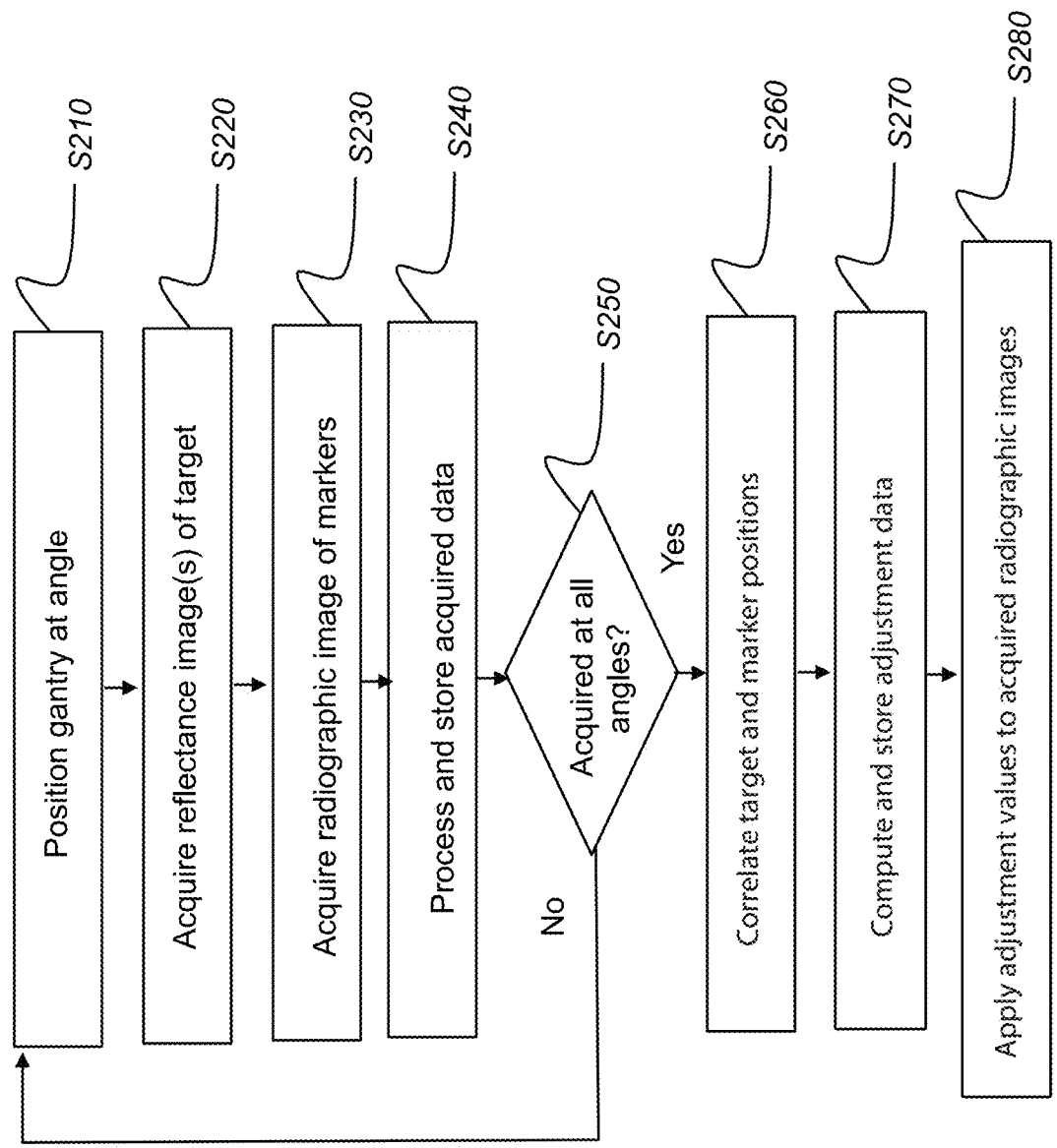

US 10,492,755 B2

CALIBRATION PHANTOM COMPRISING A REFLECTANCE CALIBRATION TARGET AND A PLURALITY OF RADIO-OPAQUE MARKERS

CROSS REFERENCE TO RELATED APPLICATIONS

This application claims the benefit of provisionally filed U.S. Ser. No. 62/361,534, filed on Jul. 13, 2016, entitled "CALIBRATION PHANTOM" in the names of Yuan Lin and William J. Sehnert, incorporated herein in its entirety.

TECHNICAL FIELD

This disclosure relates, in general, to medical imaging modalities such as computed tomography (CT), tomosynthesis, cone beam computed tomography (CBCT), dual-energy CT, magnetic resonance imaging (MRI), positron emission tomography (PET), and the like. In particular, the disclosure relates to a system and method to calibrate a medical imaging system and an associated surface acquisition system.

BACKGROUND

A surface acquisition system typically comprises a plurality of cameras, projectors, or lasers that can reconstruct a 3D surface model of an object using stereovision techniques, structured illumination or structured light techniques, or time-of-flight techniques. The generated 3D surface model has applications in conjunction with X-ray imaging. For example, the 3D surface characterization can be used as prior information for more accurate acquisition planning, dose estimation, and scatter estimation. In addition, real time 3D surface characterization can be used for detecting and compensating patient motion during image acquisition. 3D surface characterization can be particularly useful for correlation with radiography data where the x-ray imaging apparatus forms a volume image, such as a tomosynthesis image or CBCT image, for example.

Both the surface acquisition system and the X-ray imaging system are preferably calibrated before use. Typically, calibration is viewed as tedious and time-consuming, often without providing the accuracy needed where both surface characterization and volume imaging systems are used. In conventional practice where surface acquisition supports X-ray imaging, each system is separately calibrated, independently of the other system. Typically, for example, the two systems use different calibration phantoms. In addition, there appear to be no phantom solutions that allow calibration of the transformation parameters between surface acquisition and radiography systems.

Thus, with respect to imaging apparatus that combine the benefits of surface characterization with radiography imaging, there is a need for a phantom configured to: (i) calibrate the surface acquisition system (e.g., extrinsic and intrinsic calibration parameters of the cameras, projectors, or lasers); (ii) calibrate the X-ray imaging system (including geometric parameters of the X-ray tube and detector at different rotation angles); and (iii) calibrate the transformation parameters (e.g., rotation and translation) for registering spatial points between these two systems.

The background above is provided for general overview information and is not intended to be used as an aid in determining the scope of the claimed subject matter. The invention is defined by the claims.

SUMMARY

Certain embodiments described herein address the need for calibration of imaging apparatus that provide both contour imaging and a corresponding radiographic or other volume image. To overcome limitations of existing approaches, the present disclosure describes a calibration phantom and calibration approach that correlate surface characterization with internal structure for a patient or other subject.

These aspects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an embodiment of the present disclosure, there is provided a calibration phantom comprising: a surface having a reflectance calibration target with a pattern that is indicative of one or more spatial reference positions; and a plurality of radio-opaque markers disposed on or in the phantom and positionally correlated to the one or more spatial reference positions of the reflectance calibration target.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 3A-3C illustrate examples of checkerboard patterns.

FIG. 8 is a logic flow diagram showing a sequence for system calibration according to an embodiment of the present disclosure.

DETAILED DESCRIPTION OF THE EMBODIMENTS

Figure 1:
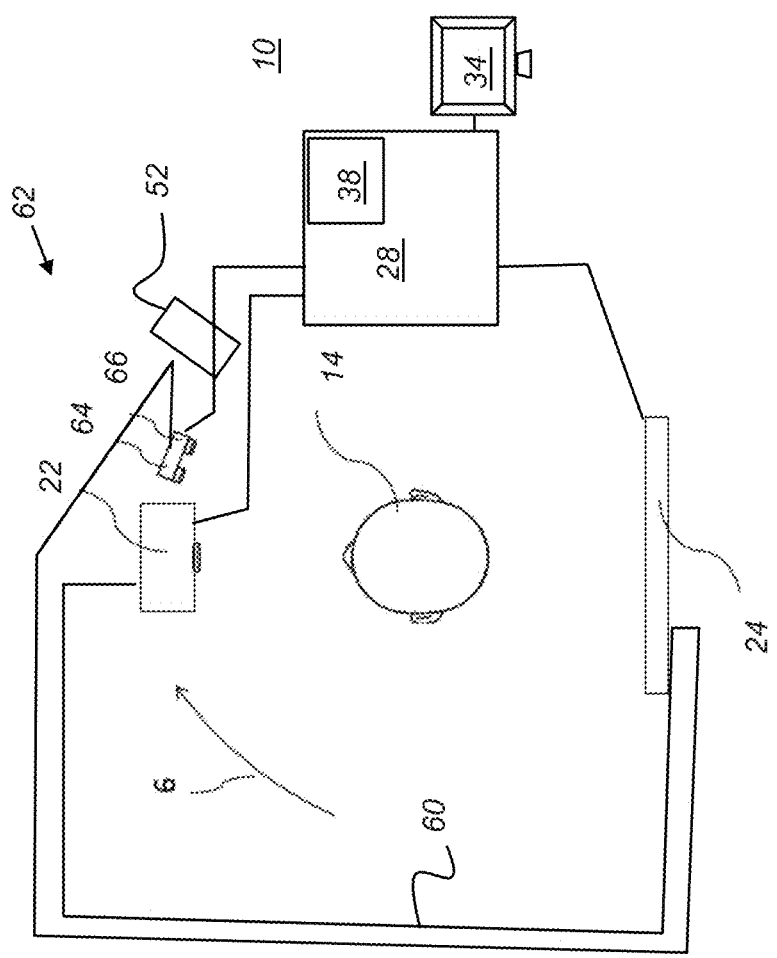
FIG. 1 is a top view schematic diagram of a CBCT imaging apparatus using a rotational gantry for simultaneously acquiring surface contour data using a surface contour acquisition device during projection data acquisition with an X-ray tube and detector.

The following is a detailed description of the embodiments of the invention, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the object that is imaged, such as the "subject patient", for example.

In the context of the present disclosure, "volume image content" describes the reconstructed image data for an imaged subject, generally stored as a set of voxels. Image display utilities use the volume image content in order to display features within the volume, selecting specific voxels that represent the volume content for rendering a particular slice or view of the imaged subject. Thus, volume image content is the body of resource information that is obtained from a radiographic or other volume imaging apparatus such as a CT, CBCT, MDCT, MRI, PET, tomosynthesis, or other volume imaging device that uses a reconstruction process and that can be used to generate depth visualizations of the imaged subject.

Examples given herein that may relate to particular anatomy or imaging modality are considered to be illustrative and non-limiting. Embodiments of the present disclosure can be applied for both 2D radiographic imaging modalities, such as radiography, fluoroscopy, or mammography, for example, and 3D imaging modalities, such as CT, MDCT, CBCT, tomosynthesis, dual energy CT, or spectral CT.

In the context of the present disclosure, the term "volume image" is synonymous with the terms "3 dimensional image" or "3D image". The phrase "reflectance imaging" refers to camera imaging that uses reflected light content for image formation and acquisition. The reflectance image used for calibration herein is obtained from a calibration target. The radiographic image that is used for calibration herein is obtained from markers provided on or within the phantom.

In the context of the present disclosure, a radiographic projection image, more simply termed a "projection image" or "x-ray image", is a 2D image formed from the projection of x-rays through a subject. In conventional radiography, a single projection image of a subject can be obtained and analyzed. In volume imaging such as CT, MDCT, and CBCT imaging, multiple projection images are obtained in series, then processed to combine information from different perspectives in order to form image voxels.

In the context of the present disclosure, the equivalent terms "surface contour imaging", "surface modeling", "surface contour characterization", or "3D surface imaging" relate to forming a model or image of the surface contour of a subject, characterizing the overall volume of the subject according to its outer surface shape, but not necessarily defining internal features beneath the skin surface. Surface contour imaging techniques include methods that use reflectance images, such as those obtained from reflectance of visible light or near-infrared light from the surface, as described in more detail subsequently. Surface contour imaging algorithms can be used to form a surface model, reconstructed from structured illumination imaging or from other types of imaging input obtained from the reflectance 2D images.

Two different types of calibration sequences are typically used to maintain a radiographic imaging apparatus such as a CBCT or tomosynthesis system in order to obtain acceptable imaging quality:

(i) quantitative calibration, for measuring and calibrating system response according to Hounsfield values that relate to radiation density and absorption. This type of calibration taught, for example, in WO 2013/185011 by Siewerdsen et al. using calibration phantoms.

(ii) geometric calibration that maintains pixel-by-pixel registration for each acquired image and compensates for mechanical drift and shifting due to weight, movement, and other factors.

Embodiments of the present disclosure are directed to apparatus and methods for geometric calibration (ii), providing solutions that can be particularly useful with volume imaging apparatus such as a CBCT system that is supported by a contour imaging system.

Reference is made to U.S. Ser. No. 15/165,159 titled SYSTEM AND METHOD FOR MOTION ARTIFACTS REDUCTION filed May 26, 2016 to Lin et al, now issued as U.S. Pat. No. 10,034,648 B2 on Jul. 31, 2018, incorporated herein in its entirety. This reference describes a system for reconstructing a 3D volume, comprising: (i) a surface acquisition system comprising a light source and an image sensor for characterizing the surface contour of a patient; and (ii) an X-ray imaging system for acquiring X-ray projection data of the patient from a plurality of angular positions. The Lin et al. disclosure is silent with respect to a phantom that supports geometric calibration of the surface acquisition and X-ray imaging systems.

FIG. 1 shows a top view component configuration for one of various CT imaging apparatus 10 configurations for acquiring both surface contour and reconstructed volume image data. FIG. 1 shows an arrangement using a rotational gantry 60 that provides a transport apparatus for orbiting x-ray source 22 and detector 24 about subject 14, along with light scanner 62 for surface contour characterization having light pattern projector 64 and camera or sensor 66. There is an optional illumination source 52 for providing a visible or near-visible illumination field or a patterned illumination. A rotation direction 6 is shown. A control logic processor 28 is in signal communication with x-ray source 22, detector 24, and light scanner 62 components for surface characterization. Control logic processor 28 can include a controller 38 that coordinates image acquisition between light scanner 62 and the CT imaging apparatus 10 in order to identify and characterize patient motion for control of image acquisition and to support subsequent processing of the x-ray projection image data. Control logic processor 28 can also include the logic for projection image processing and for volume CT image reconstruction as well as surface contour characterization, or may provide connection with one or more additional computers or processors that perform the volume or surface contour reconstruction function and display of volume imaging results, such as on a display 34. Such a configuration can be particularly suitable for medical and dental applications. For example, for dental applications, an imaging system can use a CBCT scanner combined with structured light imaging components.

Figures 2A, 2B:
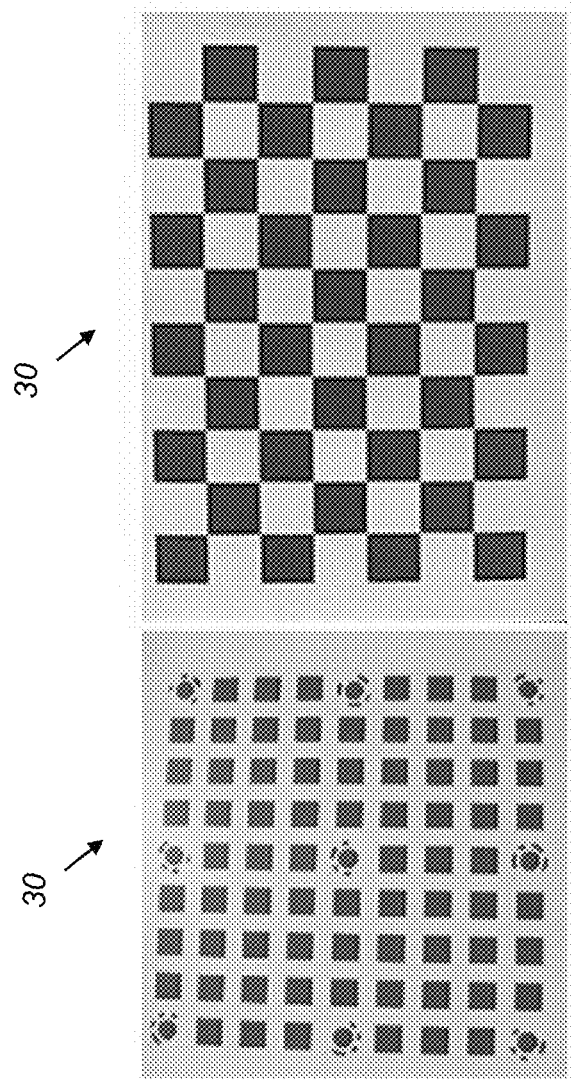
FIGS. 2A and 2B illustrate different calibration phantoms for a surface acquisition system.

For surface acquisition systems, the calibration procedure for the cameras can employ a calibration target that is a printed image attached to a surface, such as to a cardboard or other surface. Some example arrangements of conventional 2D camera calibration cards used as targets in this way are given in FIGS. 2A and 2B. Images obtained using these calibration targets 30 can be used to characterize intrinsic features of the camera device, such as the curvature of the camera lens or inherent performance characteristics of the optical system overall. Other examples using reflectance calibration targets can be found in Zhengyou Zhang, A FLEXIBLE NEW TECHNIQUE FOR CAMERA CALIBRATION, *Pattern Analysis and Machine Intelligence, IEEE Transactions on*, 2000. 22(11): p. 1330-1334, incorporated herein in its entirety.

In general, where a structured light technique is used for target illumination in the surface acquisition system, projectors or lasers are typically used as illumination sources and, preferably, are calibrated. Typically, a uniform surface is used as the target to calibrate projectors and lasers, with the assistance of auxiliary cameras. In one arrangement, the Applicants integrate a uniform surface to the phantom as the target and use structured light to form a pattern that is indicative of spatial position relative to the imaging volume. Alternately, an embodiment of the present disclosure can configure a checkerboard or other regularly repeating pattern for the calibration target. A target of this type does not require structured light, but can be perceptible under visible light illumination. Alternately, a checkerboard or other pattern can be invisible to the camera except under special calibration illumination emitted from the projector.

By way of example, FIGS. 3A-3C show some exemplary patterns 32 that can be formed on a calibration target surface. FIG. 3A illustrates a pattern that can be embodied as a red/blue checkerboard pattern 32. FIG. 3B illustrates a neutral black/white image pattern suitable for use with white light illumination. FIG. 3C shows an exemplary black/white or dark/light image pattern that can be visible with red light illumination. Other possible patterns that can be formed by illumination or formed on the calibration target can include point clouds, curves, lines, patterns, or the like. Patterns can be regular or randomized.

Reference is made to Song Zhang and Peisen S Huang, "Novel Method For Structured Light System Calibration", *Optical Engineering*, 2006. 45(8): p. 083601-083601-8, incorporated herein in its entirety.

Reference is made to Paulo J Tavares and Mário A Vaz, "Linear Calibration Procedure for the Phase-To-Height Relationship in Phase Measurement Profilometry", *Optics Communications*, 2007. 274(2): p. 307-314, incorporated herein in its entirety.

Reference is made to Xinhua Li, Da Zhang, and Bob Liu, "A Generic Geometric Calibration Method For Tomographic Imaging Systems With Flat-Panel Detectors—A Detailed Implementation Guide", *Medical Physics*, 2010. 37(7): p. 3844-3854.

For an X-ray or other radiographic imaging system, a calibration phantom for geometric calibration uses a distribution of radio-opaque markers (e.g., metal beads). Imaging the radio-opaque marker arrangement allows the geometric relationships of the X-ray tube, detector, and field of view to be accurately determined.

Figure 4A:
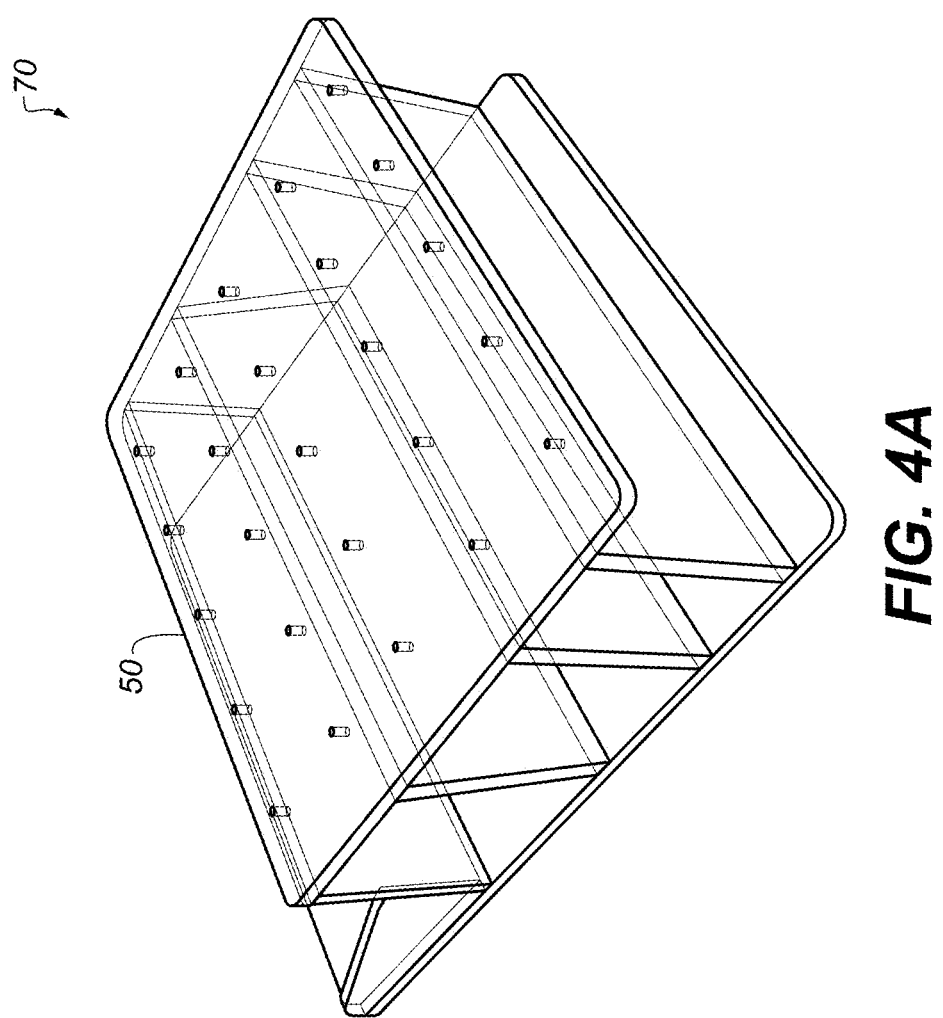
FIGS. 4A and 4B illustrate several geometric calibration phantoms.
Figure 4B:
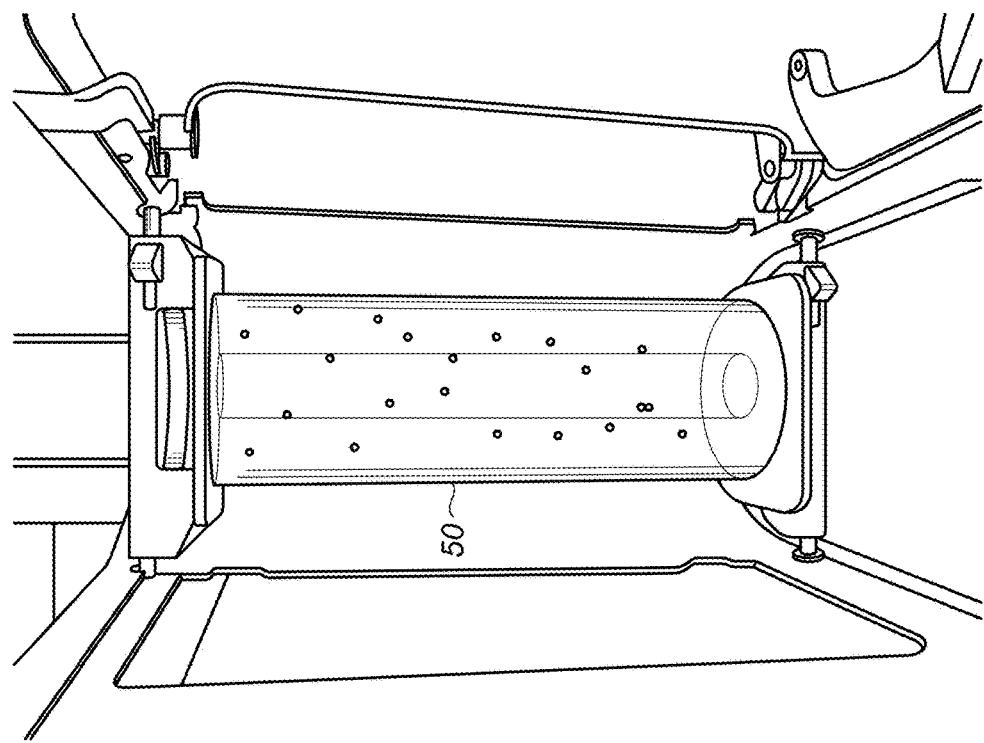

FIGS. 4A and 4B illustrate two geometric calibration phantoms that can be used for an X-ray imaging system that acquires content for volume image reconstruction. FIG. 4A shows a phantom 70 having a housing 50 that is suitable for a tomosynthesis scanner. FIG. 4B shows a phantom 72 with housing 50 for an extremity CBCT imaging scanner, such as a scanner system that is configured to acquire images of the lower leg or extended arm, for example. For use as radio-opaque markers, both phantoms 70 and 72 employ an arrangement of embedded metal beads, arranged in a pattern that is suitable for geometric calibration. Other appropriate types of opaque markers can be used for alternative imaging systems.

According to an embodiment of the present disclosure, a dual-purpose calibration phantom is provided, having:
 (i) a surface with a pattern or other calibration target for reflectance imaging, such as for image acquisition using a camera; and
 (ii) a distribution with a number of radio-opaque markers that can be imaged on an x-ray film or other x-ray detector medium.

In embodiments of the phantom given herein, radio-opaque metal beads used as markers for radiographic calibration are either embedded within or sandwiched between corresponding patterns or a surface arrangement used as calibration targets for surface imaging. Radiographic calibration uses the marker arrangement and spatial relationships of metal beads or other radio-opaque features. As noted previously, visible patterns used as part of the calibration target for surface contour imaging with reflectance light can be of various types, using patterned targets ranging from those formed by patterned light projected onto a uniform grayscale surface to broadband illumination that is directed to a surface with checkerboard patterns and a range of other possible variegated designs. For acquiring surface contour information, some type of patterning is generally used for obtaining image content using the phantom.

To compute the transformation parameters (i.e., rotation and translation) between the surface contour imaging system components and the X-ray imaging system, the Applicants can measure the coordinates of the same spatial location relative to the two systems. This can be achieved by adding some additional beads or other radio-opaque marker features, mounted or otherwise attached to predetermined locations of the checkerboard pattern, which can then be simultaneously registered by the radiographic and reflectance imaging systems. Given the resulting coordinates of the two point clouds from the two systems, various algorithms can be applied to calculate the transformation parameters for coordinate registration. This includes, for example, algorithms for point set registration, identifying a suitable spatial transformation for correlating two related point sets, such as coherent point drift (CPD).

Figure 5B:
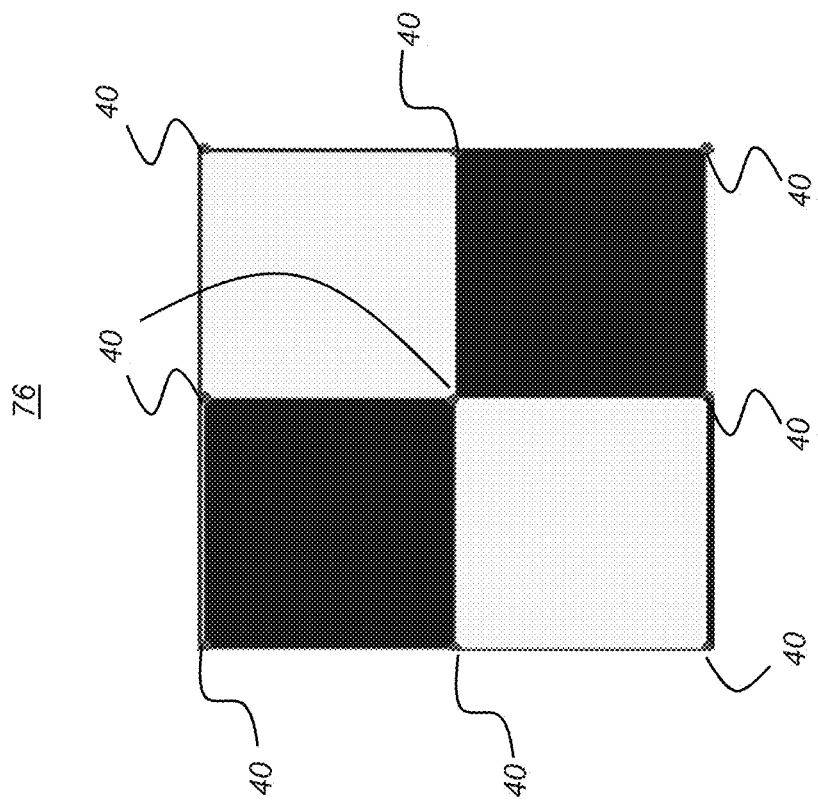
FIG. 5B shows a checkerboard marker which corresponds with FIG. 5A.
Figure 5A:
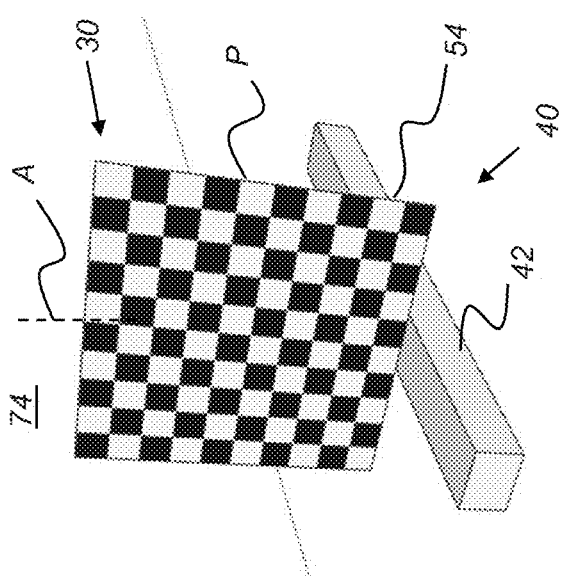
FIG. 5A shows an exemplary calibration phantom.

FIG. 5A shows an exemplary calibration phantom 74 that can be used with CT imaging apparatus 10 in FIG. 1, wherein the target 30 is positioned on one plane P, surface 54. Phantom 74 has a base 42 for seating within rotational gantry 60. The phantom 74 can be stationary. Alternately, the phantom 74 can be mounted on base 42 having a plurality of motors, such that surface 54 can rotate or sweep through the entire field of view to calibrate more points within the field of view. The planar surface 54 of phantom 74 rotates about an axis A and can sweep or rotate, synchronous with rotational gantry 60 rotation, to cover the entire volume of interest. Radio-opaque markers 40 disposed within phantom 74 may or may not be visible to the reflectance imaging apparatus.

FIG. 5B shows a portion of a checkerboard on a surface for a phantom 76 with radio-opaque markers 40, wherein the black and white checkerboard target is used to provide a reflectance image for camera calibration, such as to measure lens distortion, and wherein the radio-opaque markers 40, used to calibrate the X-ray imaging geometry, are metallic or ceramic beads that are positioned at one or more checkerboard corners. With the arrangement shown in FIG. 5B, radio-opaque markers 40 can be registered with the reflectance image, since it is clear where the radio-opaque markers 40 are positioned relative to visible features of the phantom 76 that form the reflectance target. However, there can be some confusion as to the correspondence between a particular radio-opaque marker and visible features that correspond to the position of the radio-opaque marker relative to the target.

Figure 6C:
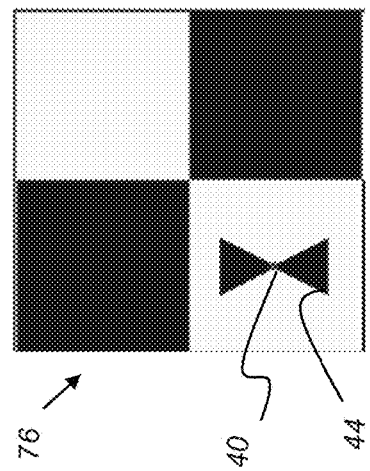
FIGS. 6A-6C illustrate exemplary markers in accordance with the present disclosure.
Figure 6B:
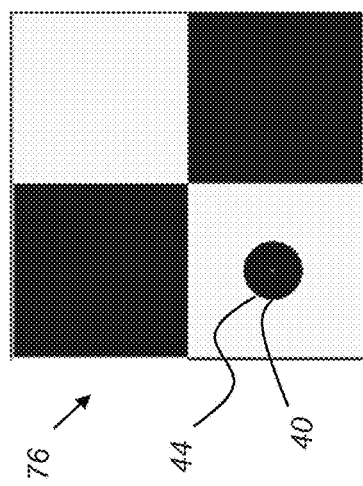
Figure 6A:
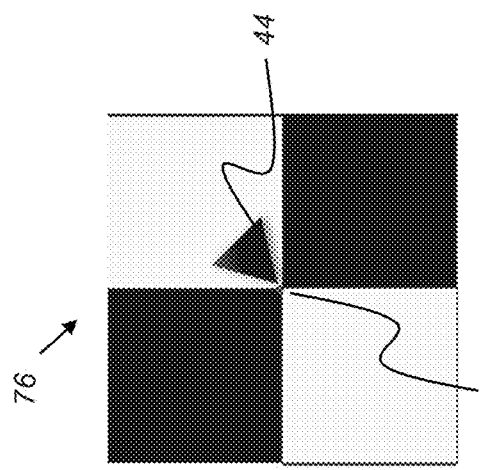

FIGS. 6A-6C illustrate examples of different types of visible indicators 44 on the reflectance calibration target that point to radio-opaque markers 40, allowing simultaneous registration of the same phantom location to the reflectance calibration or surface acquisition system and the radiographic or X-ray imaging system.

In FIG. 6A, an indicator 44 on the target serves as a pointer to the location of marker 40, a radio-opaque bead in the middle of the checkerboard intersection point for the portion of phantom 76 shown.

In FIG. 6B, indicator 44 is a metal bead that serves as radio-opaque marker 40. According to an alternate embodiment of the present disclosure, indicator 44 can be a reference indicium that can be used by image analysis software to register the reflectance image with one or more markers 40 that are associated with phantom 76. Thus, for example, a pattern of indicators 44 can serve as a guide for orientation of the reflectance surface contour and radiographic images obtained from phantom 76.

FIG. 6C shows another arrangement with indicators 44 that pinpoint the location of radio-opaque marker 40 within phantom 76.

FIGS. 7A-7F illustrate a series of possible/alternative/exemplary designs/configurations of the phantom of the present disclosure.

Figure 7B:
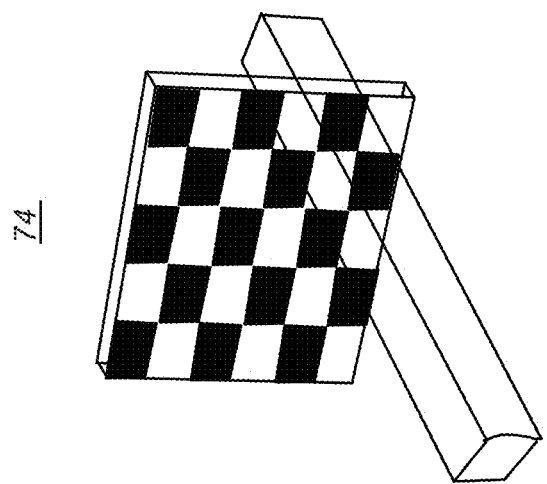
FIGS. 7A-7F illustrate a series of exemplary designs of the phantom in accordance with the present disclosure.
Figure 7A:
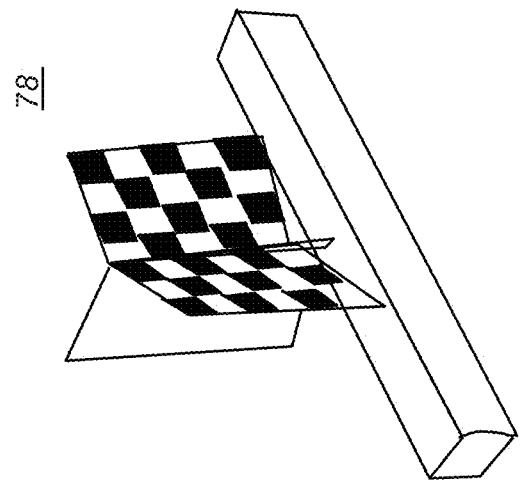

FIG. 7A shows a planar phantom 74 similar to that shown in FIG. 5A.

FIG. 7B shows a rotating phantom 78 with multiple planar surfaces. These surfaces can be stationary or may rotate along with the gantry or other mechanism that moves the x-ray source and detector.

Figure 7D:
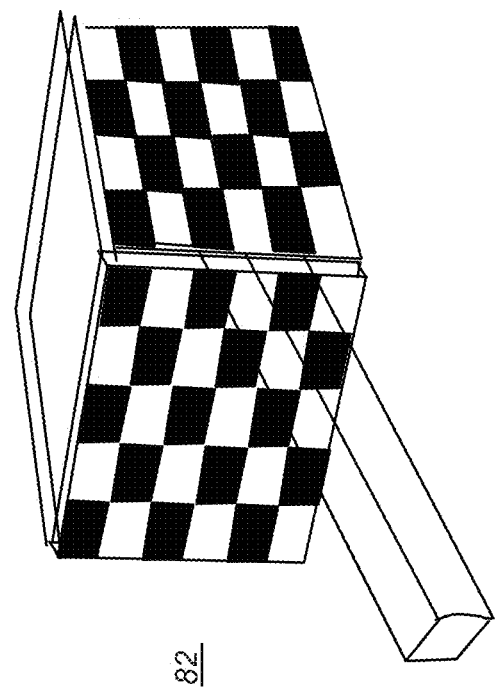
Figure 7C:
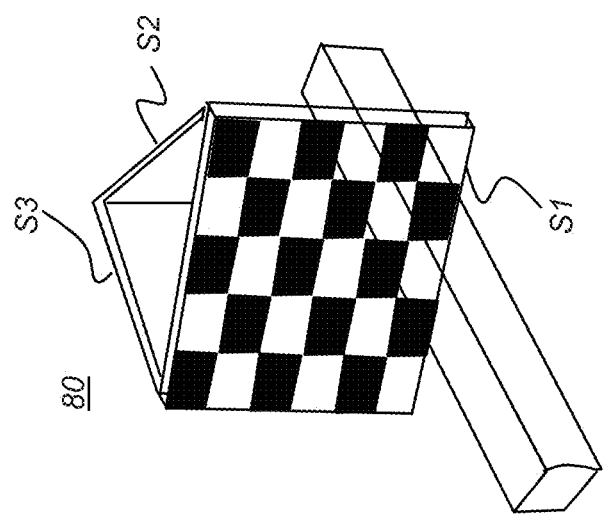

FIG. 7C shows a multiple surface phantom 80 in an alternate configuration. The multiple surface phantom 80 has a reflectance calibration target with three surfaces S1, S2, and S3.

FIG. 7D shows a multiple surface phantom 82 in an alternate configuration.

Figure 7F:
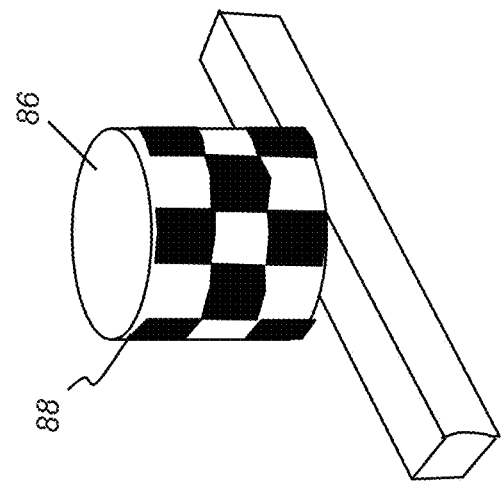
Figure 7E:
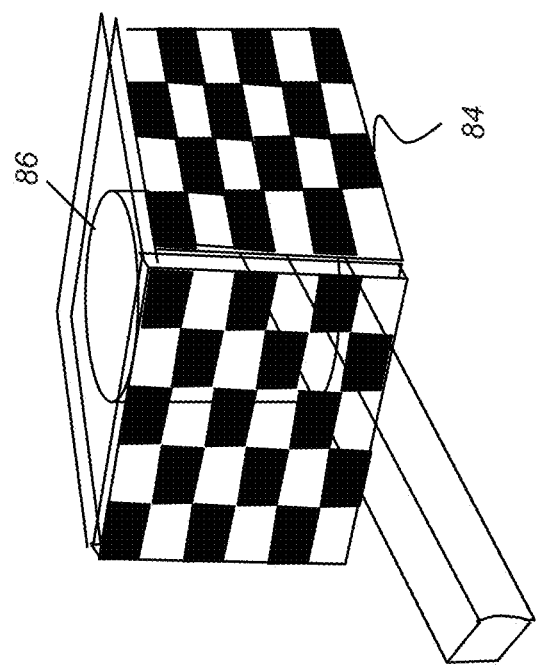

FIG. 7E shows a multi-surface phantom 84 that acts as a sleeve over an existing CT phantom 86.

FIG. 7F shows a circular cylindrical phantom 88 that acts as a sleeve over CT phantom 86.

The logic flow diagram of FIG. 8 shows an overall sequence for system calibration according to an embodiment of the present disclosure. Image acquisition repeats in a loop for a set of steps S210, S220, S230, S240, and S250. In a positioning step S210, the rotational gantry 60 or other angular positioning device that couples x-ray source 22 and detector 24 movement moves to the next angular position for calibration imaging. A target acquisition step S220 and radiographic acquisition step S230 can be executed simultaneously or in sequence, in either order, in order to obtain both the needed reflectance image and radiographic image. A processing step S240 then processes and stores the acquired data. A test step S250 determines whether the calibration series has been completed or if it is necessary to advance the rotational gantry 60 to the next angle for a repeat of the loop sequence. When image acquisition at all angles has taken place, a correlation step S260 performs the needed computation to determine the corresponding spatial positions and offset, if any, between the reflectance and radiographic images. A computation step S270 then performs the needed adjustment computation and can generate a transform matrix or other computational tool in order to perform the needed adjustment for displaying a geometrically calibrated image. An adjustment step S280 then applies the computations from step S270 to correct the calibration for subsequent imaging. The imaging apparatus then displays radiographic images conditioned by the transformation parameters.

Figure 9:
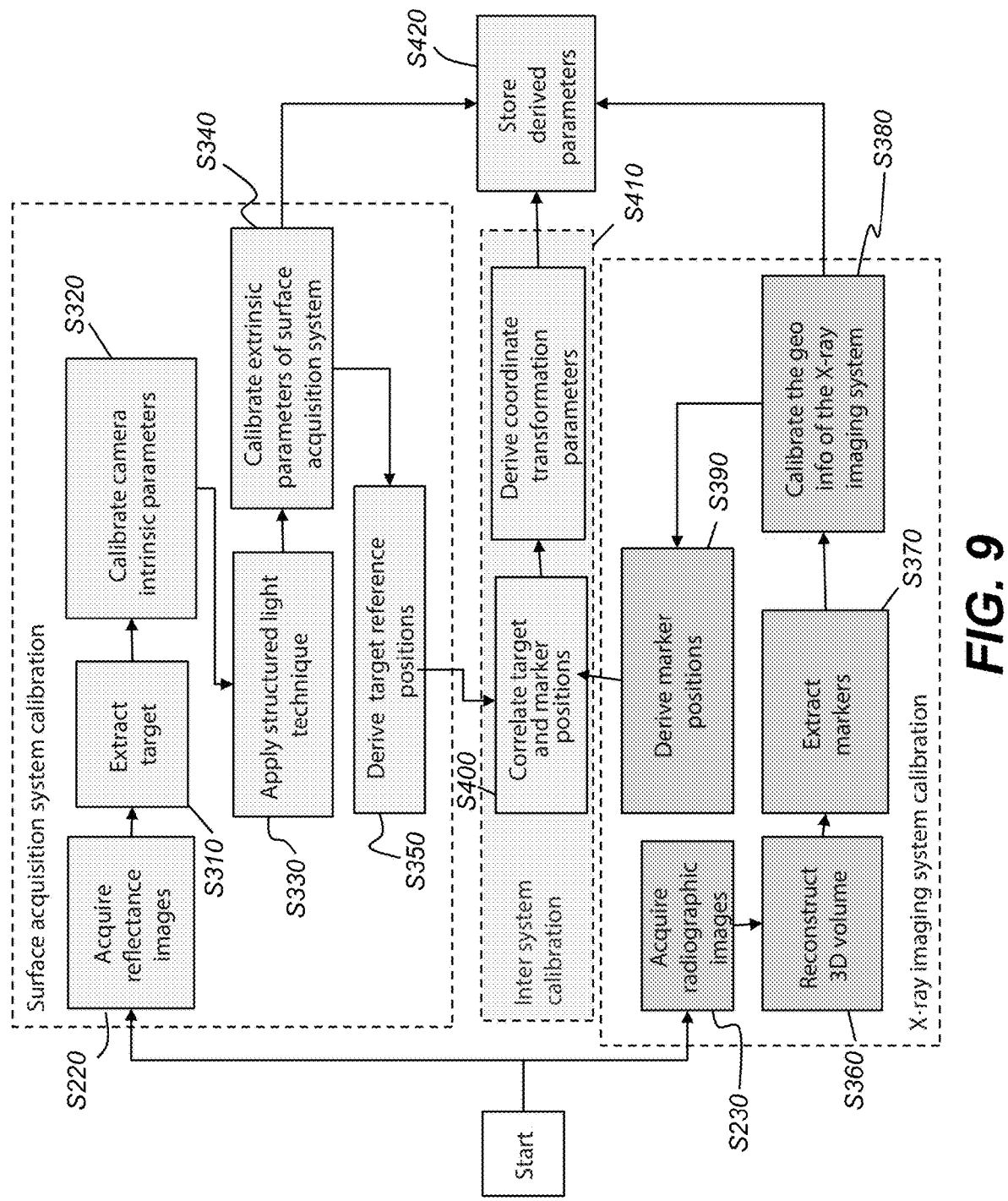
FIG. 9 is a logic flow diagram that provides additional detail of the processing sequence for generating the adjustment transformation used for inter-system calibration.

The logic flow diagram of FIG. 9 provides additional detail of the processing sequence for generating the adjustment transformation used for inter-system calibration. In the top portion of the FIG. 9 logic flow is the sequence for target acquisition using reflectance imaging. Target acquisition step S220 acquires the reflectance images, such as structured light images or other images of a patterned calibration target. A target extraction step S310 is executed, in which the target is identified and extracted for analysis and measurement. A camera calibration step S320 then provides calibration data for intrinsic parameters of the reflectance imaging apparatus, such as lens curvature or other inherent distortion, for example. An optional illumination step S330 uses structured light illumination to acquire reflectance calibration data; alternately, a highly patterned calibration target can be used, such as those shown in FIGS. 6A-7F, along with flat field illumination. A calculation step S340 calculates extrinsic parameters of the surface acquisition apparatus according to the target measurements. A derivation step S350 then derives spatial reference positions from the target according to the calculated measurement data.

The x-ray system calibration sequence of FIG. 9 begins with radiographic acquisition step S230. A reconstruction step S360 then reconstructs 3D volume data from the set of acquired radiographic images. A marker extraction step S370 extracts the pattern of radio-opaque markers from the calibration target. A calculation step S380 performs the needed calculations for geometric calibration of the x-ray imaging apparatus. A derivation step S390 derives positions of radio-opaque markers from the acquired content. Then, as part of the inter-system calibration processing, a correlation step S400 correlates the calculated target and marker positions. A transform generation step S410 generates the needed transform to correlate the adjustment between reflectance and radiographic imaging apparatus. A transform storage step S420 then stores the generated transforms for subsequent use.

It is noted that the surface and x-ray acquisition and processing sequences of FIG. 9 can be executed simultaneously or in any suitable sequence While the fabrication and use of various embodiments of the phantom of the present disclosure are discussed in detail below, it is appreciated that this disclosure provides various applicable inventive concepts which can be embodied in a variety of specific contexts. The specific embodiments described herein are merely illustrative of specific ways to make and use the disclosure and do not delimit the scope of any invention.

Particular features the phantom are now described.

The phantom is preferably comprised of a housing and a plurality of markers. The housing and the markers can be combined together to calibrate the intrinsic and extrinsic parameters of a surface acquisition system and an X-ray imaging scanner. The housing can be made of plastic, paperboard, glass, metal, or the like.

The imaging apparatus of the present invention preferably includes two systems: a surface acquisition system that acquires a reflectance image and an X-ray imaging system. The surface acquisition system can include a plurality of cameras, projectors, or lasers.

Radio-opaque markers are preferably markers configured to calibrate the cameras of the surface acquisition system. Markers can be coordinated with reference content from the reflectance imaging apparatus, such as checkerboard markers, point clouds, curves, lines, patterns, and the like. The markers are preferably markers configured to calibrate the projectors of the surface acquisition system, such as uniform white board or boards with markers that are invisible to the cameras under the certain light conditions of the projectors.

The markers are preferably markers configured to calibrate the geometry of the X-ray imaging system, such as beads made of metals, plastics, or holes.

The markers are preferably markers configured to be simultaneously registered by the cameras of the surface acquisition system and the X-ray imaging system. The markers are preferably markers configured to compute the transformation parameters between the surface acquisition system and the X-ray imaging system.

The phantom can be mounted on base 42 having a plurality of motors, such that it can rotate or sweep through the entire field of view to calibrate more points within the field of view.

Accordingly, there is described a single calibration phantom configured to: (i) calibrate a surface acquisition system; (ii) calibrate a X-ray imaging system; and (iii) calibrate transformation parameters for registering the points between the surface acquisition system and the X-ray imaging system.

Accordingly, there is described a calibration method, comprising: providing a single calibration phantom; and using the single calibration phantom, (i) calibrating a surface acquisition system; (ii) calibrating an X-ray imaging system; and (iii) calibrating transformation parameters for registering points between the surface acquisition system and the X-ray imaging system.

The calibration phantom comprises a housing and a plurality of markers, wherein the markers are employed to calibrate the intrinsic and extrinsic parameters of an X-ray imaging scanner, wherein the X-ray imaging scanner of includes two systems: a surface acquisition system and an X-ray imaging system.

In at least one arrangement, the markers are configured to calibrate at least one camera of the surface acquisition system.

In at least one arrangement, the markers are checkerboard markers, point clouds, curves, lines, patterns, or the like.

In at least one arrangement, the markers are configured to calibrate at least one projector of the surface acquisition system, such as uniform white board or boards with markers that are invisible to a camera under the certain light conditions of the at least one projector.

In at least one arrangement, the markers are configured to calibrate geometry of the X-ray imaging system, such as beads made of metals, plastics, or holes.

In at least one arrangement, the markers are configured to be simultaneously registered by at least one camera of the surface acquisition system and the X-ray imaging system.

In at least one arrangement, the markers are configured to compute at least one transformation parameter between the surface acquisition system and the X-ray imaging system.

Consistent with one embodiment, the present invention utilizes a computer program with stored instructions that control system functions for image acquisition and image data processing for image data that is stored and accessed from external devices or an electronic memory associated with acquisition devices and corresponding images. As can be appreciated by those skilled in the image processing arts, a computer program of an embodiment of the present invention can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present invention, including an arrangement of networked processors, for example.

The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

The invention has been described in detail, and may have been described with particular reference to a suitable or presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A calibration phantom comprising:
    a surface having a reflectance calibration target with a pattern indicative of one or more spatial reference positions; and
    a plurality of radio-opaque markers positionally correlated to the one or more spatial reference positions of the reflectance calibration target, wherein one or more of the plurality of radio-opaque markers are disposed on the reflectance calibration target.

2. The calibration phantom of claim 1, wherein the pattern includes a checkerboard pattern.

3. The calibration phantom of claim 2, wherein one or more of the plurality of radio-opaque markers are positioned at intersection points along the reflectance calibration target.

4. The calibration phantom of claim 1, wherein the pattern provides point clouds, curves, or lines.

5. The calibration phantom of claim 1, wherein the surface is configured to reflect the pattern, the pattern comprising projected light from an illumination source.

6. The calibration phantom of claim 1, wherein the pattern of the reflectance calibration target is perceptible to a viewer.

7. The calibration phantom of claim 1, wherein one or more of the plurality of radio-opaque markers comprise metal beads.

8. A calibration phantom, comprising:
    a housing including a surface;
    a calibration target on a selected area of the surface, the calibration target formed as a patterned image using visible or near-visible illumination; and
    a plurality of radio-opaque markers spatially disposed at predetermined positions within the selected area.

9. The calibration phantom of claim 8, wherein the patterned image comprises a regularly repeating pattern.

10. The calibration phantom of claim 8, wherein the patterned image comprises pattern features that point to at least one of the plurality of radio-opaque markers.

11. An imaging system comprising:
    an x-ray source;
    a radiographic detector configured to acquire one or more x-ray images of a subject positioned between the x-ray source and the radiographic detector;
    a camera coupled to the x-ray source,
    wherein the camera is configured to acquire one or more reflectance images of a surface of the subject; and
    a calibration phantom positioned between the x-ray source and the radiographic detector,
    the calibration phantom comprising:
        a surface having a reflectance pattern thereon, the reflectance pattern visible on a selected area of the surface, the reflectance pattern configured to be captured by the camera; and
        one or more radio-opaque markers within the selected area, the one or more radio-opaque markers configured to be captured by the radiographic detector.

12. The imaging system of claim 11, wherein the reflectance pattern comprises a regularly repeating pattern.

13. The imaging system of claim 11, wherein the reflectance pattern comprises pattern features positioned to point to at least one of the one or more radio-opaque markers.

14. A method for calibration of a radiographic imaging apparatus, the method executed at least in part by a computer, comprising:
    providing a calibration target having a surface;
    projecting a visible pattern on the surface of the calibration target;
    acquiring a reflectance image of the visible pattern;
    processing the acquired reflectance image to derive one or more spatial reference positions from the calibration target based on the visible pattern;
    acquiring a radiographic image of one or more radio-opaque markers disposed within the visible pattern on the surface of the calibration target;
    processing the acquired radiographic image to derive one or more positions of the one or more radio-opaque markers;
    correlating the one or more spatial reference positions from the calibration target with the one or more positions of the one or more radio-opaque markers and generating transformation parameters; and
    displaying, storing, or transmitting a radiographic image conditioned by the transformation parameters.

15. The method of claim 14, wherein acquiring the reflectance image of the calibration target comprises acquiring an image generated using structured illumination.

16. The method of claim 14, wherein acquiring the radiographic image of the one or more radio-opaque markers comprises acquiring a projection image from a cone-beam computed tomography apparatus.

17. The method of claim 14, further comprising projecting a regularly repeating visible pattern on the surface of the calibration target.

18. The method of claim 14, further comprising disposing at least one of the one or more radio-opaque markers at an intersection point of the visible pattern on the surface of the calibration target.

19. The method of claim 14, further comprising forming features in the visible pattern of the calibration target that point to at least one of the one or more radio-opaque markers.

* * * * *